United States Patent
Baldus et al.

(10) Patent No.: US 7,924,150 B2
(45) Date of Patent: Apr. 12, 2011

(54) SAFE IDENTIFICATION AND ASSOCIATION OF WIRELESS SENSORS

(75) Inventors: Heribert Baldus, Aachen (DE); Thomas Falck, Aachen (DE); Karin Klabunde, Aachen (DE); David Sanchez Sanchez, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 657 days.

(21) Appl. No.: 11/718,554

(22) PCT Filed: Nov. 4, 2005

(86) PCT No.: PCT/IB2005/053612
§ 371 (c)(1),
(2), (4) Date: May 3, 2007

(87) PCT Pub. No.: WO2006/048840
PCT Pub. Date: May 11, 2006

(65) Prior Publication Data
US 2009/0062626 A1 Mar. 5, 2009

Related U.S. Application Data

(60) Provisional application No. 60/625,935, filed on Nov. 8, 2004.

(51) Int. Cl.
*G08B 1/08* (2006.01)
(52) U.S. Cl. ............... 340/539.12; 341/174; 375/130
(58) Field of Classification Search ............ 340/539.12; 341/174; 375/130
See application file for complete search history.

(56) References Cited

U.S. PATENT DOCUMENTS

| | | | | |
|---|---|---|---|---|
| 5,348,008 A | * | 9/1994 | Bornn et al. | 600/301 |
| 5,604,503 A | * | 2/1997 | Fowler et al. | 342/378 |
| 5,607,457 A | * | 3/1997 | Schuller | 607/9 |
| 5,701,894 A | * | 12/1997 | Cherry et al. | 600/300 |
| 6,135,966 A | * | 10/2000 | Ko | 600/481 |
| 6,238,338 B1 | * | 5/2001 | DeLuca et al. | 600/300 |
| 6,287,252 B1 | * | 9/2001 | Lugo | 600/300 |

(Continued)

FOREIGN PATENT DOCUMENTS
WO 2004089201 A1 10/2004

OTHER PUBLICATIONS

Du, W., et al.; A key management scheme for wireless sensor networks using deployment knowledge; 2004; Conf. of IEEE Computer and Communications Societies; vol. 1; pp. 586-597.

(Continued)

*Primary Examiner* — George A Bugg
*Assistant Examiner* — Bradley E Thompson (57) ABSTRACT

A wireless sensor network for wirelessly monitoring a medical subject includes a plurality of sensor nodes (22, 24, 26, 122, 124, 126). Each sensor node includes a wireless transceiver (46) for sending and receiving wireless messages, a sensor (40, 42, 130, 132, 140, 142) monitoring a characteristic of the medical subject, and a processor (50). The processor is programmed to at least perform an authentication method including: (i) acquiring sensor data via the sensor for a predetermined time (76) responsive to receiving a wireless trigger message; (ii) storing an association code (60, 150, 152, 160, 162) computed from the acquired sensor data; and (iii) authenticating a subsequently received wireless message containing an association code tag by comparing the association code tag with the stored association code. The processor further attaches the stored association code as the association code tag in messages sent to other sensors.

21 Claims, 4 Drawing Sheets

U.S. PATENT DOCUMENTS

| | | | |
|---|---|---|---|
| 6,324,505 | B1 * | 11/2001 | Choy et al. .................... 704/230 |
| 6,527,711 | B1 | 3/2003 | Stivoric et al. |
| 2002/0045836 | A1 | 4/2002 | Alkawwas |
| 2002/0065457 | A1 | 5/2002 | Kuth |
| 2002/0075163 | A1 * | 6/2002 | Smith et al. .............. 340/870.16 |
| 2002/0107679 | A1 * | 8/2002 | Roelofs .......................... 703/22 |
| 2002/0109621 | A1 * | 8/2002 | Khair et al. ................... 341/174 |
| 2003/0229514 | A2 | 12/2003 | Brown |
| 2004/0039261 | A1 * | 2/2004 | Bardy ........................... 600/300 |
| 2004/0078219 | A1 * | 4/2004 | Kaylor et al. ..................... 705/2 |
| 2004/0107366 | A1 * | 6/2004 | Balfanz et al. ................ 713/201 |
| 2006/0034348 | A1 * | 2/2006 | Schaefer et al. .............. 375/130 |
| 2006/0074713 | A1 * | 4/2006 | Conry et al. ...................... 705/2 |
| 2007/0016069 | A1 * | 1/2007 | Grunwald et al. ............ 600/468 |
| 2008/0298603 | A1 * | 12/2008 | Smith ............................. 381/67 |
| 2009/0062626 | A1 * | 3/2009 | Baldus et al. ................. 600/301 |
| 2009/0076346 | A1 * | 3/2009 | James et al. .................. 600/301 |
| 2009/0177101 | A1 * | 7/2009 | Hersh et al. ................... 600/511 |

OTHER PUBLICATIONS

Lamprinos, I. E., et al.; A low power medium access control protocol for wireless medical sensor networks; 2004; IEEE; vol. 3; pp. 2129-2132.

Cherukuri, et al.; A biometric based approach for securing communication in wireless networks of biosensors implanted in the human body; 2003; Proc. Intl. Conf. Parallel Processing Workshops.

* cited by examiner

SAFE IDENTIFICATION AND ASSOCIATION OF WIRELESS SENSORS

CROSS REFERENCE TO RELATED APPLICATIONS

This application claims the benefit of U.S. provisional application Ser. No. 60/625,935 filed Nov. 8, 2004, which is incorporated herein by reference.

The following relates to the medical monitoring arts. It finds particular application in wireless autonomous sensor networks, and will be described with particular reference thereto. More generally, it finds application in wireless medical sensors and in wireless monitoring of medical patients.

A patient admitted to a hospital typically arrives at a hospital emergency room, where the patient is connected with various vital signs monitoring sensors, such as an electrocardiographic (ECG) sensor, a blood pressure sensor, a blood oxygen saturation ($SaO_2$) sensor, and so forth. These vital signs are monitored by emergency room personnel and are used to diagnose the patient's condition and determine whether the patient should be admitted and, if so, into which medical unit the patient should be directed (such as the intensive care unit, cardiac care unit, respiratory care unit, general admittance, or so forth).

The patient is then transferred from the emergency room to the appropriate medical care unit or other hospital area. This typically entails disconnecting the vital signs monitoring sensors, transporting the patient to the new location, and connecting the patient to a new set of vital signs monitoring sensors. During the move, the patient may be left unmonitored by any electronic sensors. Also, there may be a delay in communicating the vital signs monitoring records acquired in the emergency room to the new location or, worse yet, the monitoring records from the emergency room may be lost. If the patient was medicated or otherwise treated while in the emergency room, comparison of recorded vital signs acquired in the emergency room before medication or treatment with the patient's current vital signs monitored at the new location can be useful in assessing the effectiveness of the medication or treatment.

These problems associated with transporting the patient from the emergency room to a medical unit are repeated each time the patient is moved. Electronic patient monitoring is interrupted each time the patient is transported to a testing facility, a step-down unit, a general care wing of the hospital, or other location.

To provide uninterrupted electronic patient monitoring, even during patient transport, there is interest in developing robust wireless autonomous sensor networks, which include a plurality of "smart" wireless sensors having the capability to operate and to store sensor data even when not connected with a monitoring station. Accordingly, the wireless autonomous sensor network remains connected to the patient during patient transport and continues to collect and store sensor data. When the patient arrives at a new location, the autonomous sensor network wirelessly connects with a local monitoring station through which the current output of the sensors, and optionally also the stored sensors data, can be accessed.

One difficulty in developing a robust wireless autonomous sensor networks is the sensors association problem. A hospital or other medical facility typically has a large number of patients. When a patient is monitored by a wireless autonomous sensor network, all sensors for that patient should associate together to define an autonomous network without inadvertently associating with sensors monitoring other patients.

One way to address the association problem is to use very short range wireless communication between the sensors, so that any nearby sensors that are monitoring other patients are out of range. However, this approach is usually not feasible or reliable, because in certain situations monitored patients may be brought quite close together. For example, two monitored patients may be in the same hospital room, in adjacent beds in the emergency room unit, or so forth.

In other approaches, sensors are designated as belonging to a specific sensor network by electronically tagging each sensor of the network. For example, each sensor of the network can be assigned a common network identification number. When the sensors communicate amongst one another, the network identification number is tagged to the communication to verify that it is a communication of the network. This approach has the disadvantage of generally requiring manual intervention to assign the network identification numbers. Additionally, the approach can be prone to errors, for example if the same network identification number is assigned to two nearby networks, or if medical personnel inadvertently forget to re-assign the sensors when they are placed onto a new patient.

The following contemplates improved apparatuses and methods that overcome the aforementioned limitations and others.

According to one aspect, a wireless sensor network is disclosed for wirelessly monitoring a medical subject. The wireless sensor network includes a plurality of sensor nodes. Each sensor node includes a wireless transceiver for sending and receiving wireless messages, a sensor monitoring a characteristic of the medical subject, and a processor. The processor is programmed to at least perform an authentication method including: (i) acquiring patient vital sign data via the sensor for a predetermined time responsive to receiving a wireless trigger message; (ii) storing an association code computed from the acquired sensor data; and (iii) authenticating a subsequently received wireless message containing an association code tag by comparing the association code tag with the stored association code.

According to another aspect, a wireless sensor network method is provided, which is performed by a plurality of sensor nodes wirelessly monitoring a medical subject. The wireless sensor network method includes performing at each sensor node an authentication process including: (i) acquiring sensor data pertaining to a characteristic of the medical subject for a predetermined time responsive to a receiving wireless trigger message; (ii) storing an association code computed from the acquired sensor data; and (iii) authenticating a subsequently received wireless message containing an association code tag by comparing the association code tag with the stored association code.

One advantage resides in providing a robust wireless autonomous sensor network for medical monitoring.

Another advantage resides in substantially reduced likelihood of cross-talk between sensor networks of nearby patients.

Yet another advantage resides in enabling rapid addition and removal of sensors from an autonomous sensor network without requiring manual identification of the added sensor and without substantial disruption of operation of the sensor network.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
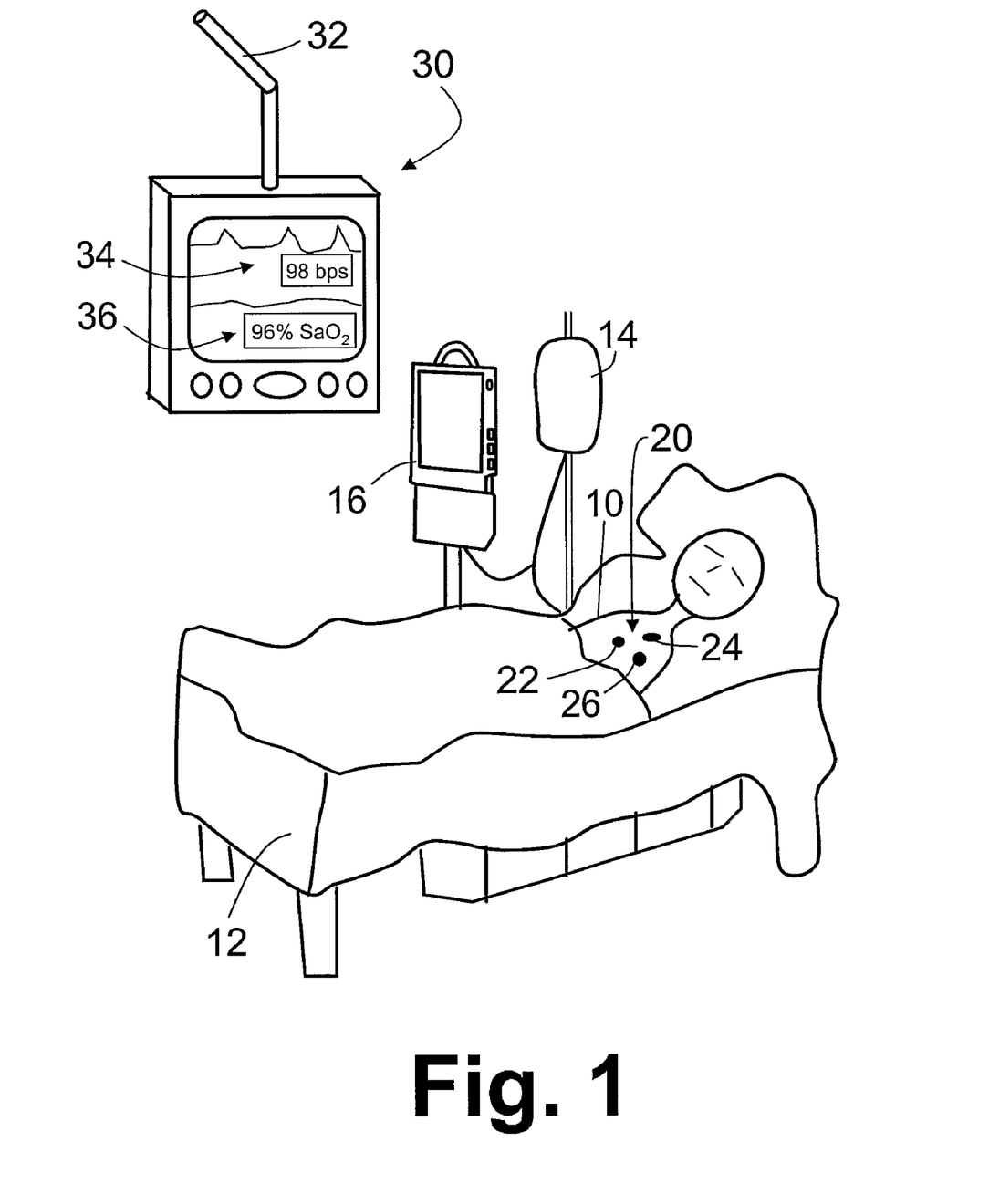
FIG. 1 illustrates an example medical monitoring situation employing a wireless autonomous sensor network.

With reference to FIG. 1, a medical patient 10 is lying on a bed 12. The illustrated patient 10 is receiving fluid intravenously from an intravenous fluid reservoir 14 controlled by an intravenous, flow monitor 16. This intravenous fluid treatment is an illustrative example; in general, the patient 10 could be receiving additional or other treatment, could be receiving medication e.g. from an automated dispenser such as a perfusion pump, or could be undergoing no treatment or medication whatsoever.

The patient 10 is monitored by a wireless sensor network 20 which in the illustrated embodiment includes three sensor nodes 22, 24, 26. More generally, the sensor network can include substantially any number of sensor nodes. The sensors 22, 24, 26 wirelessly communicate with an external monitor 30. In the illustrated embodiment the external monitor 30 is mounted on the ceiling (not shown) by an articulated mounting arm 32, and is displaying: (i) electrocardiographic (ECG) data 34; and (ii) blood oxygen saturation ($SaO_2$) data 36, both received from the sensor network 20. In general, each sensor node 22, 24, 26 includes one or more sensors for monitoring one or more vital signs or other patient characteristics, such as ECG, $SaO_2$, heart rate, respiratory rate, respiratory cycle, blood pressure, brain waves, or so forth.

Figure 2:
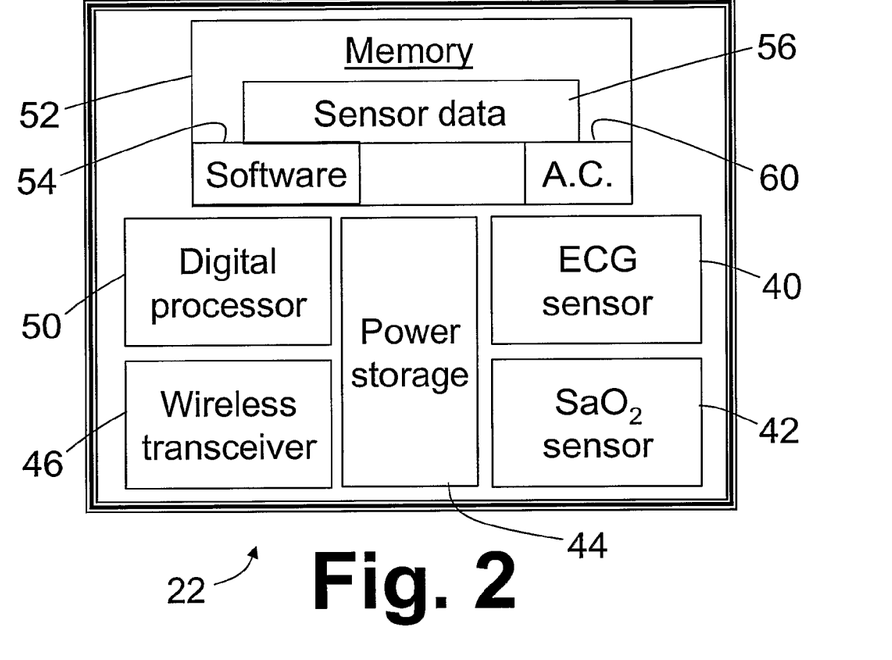
FIG. 2 diagrammatically illustrates one of the wireless sensor nodes of the wireless autonomous sensor network of FIG. 1.

With continuing reference to FIG. 1 and with further reference to FIG. 2 which diagrammatically shows the illustrative wireless sensor node 22, each sensor node 22, 24, 26 includes one or more sensors, such as the illustrative ECG sensor 40 and the illustrative $SaO_2$ sensor 42 of the sensor node 22, and further includes a power supply, such as the illustrative power supply 44 of the sensor node 22, and a wireless transceiver 46. The power supply 44 can be a rechargeable battery, storage capacitor, or other rechargeable power source, or can be a disposable battery. In some rechargeable power supply embodiments, the power supply 44 is wirelessly recharged, for example by exposure to infrared or radio frequency radiation. In other rechargeable power supply embodiments, the power supply 44 is recharged by connecting it with a battery charger. In view of the typically limited available on-board power, the wireless transceiver 46 is typically a low power, short range radio frequency transmitter that also includes radio frequency receive capability. Higher power, longer range transceivers are also contemplated, however.

In some preferred embodiments, the wireless sensor network 20 is an autonomous wireless sensor network in which the sensor nodes 22, 24, 26 communicate amongst one another and operate autonomously even in the absence of a wireless connection to the external monitor 30 or another external device. To enable autonomous monitoring, the sensor node 22 further includes a digital processor 50 and a non-volatile memory 52. A portion of the non-volatile memory 52 is allocated to storing software 54 that is executable by the digital processor 50. In some embodiments, the portion of memory storing the software 54 is read-only. In other embodiments the software is stored in read/write memory and can be updated by uploading new program code into the memory 52, for example by wirelessly receiving software updates via the wireless transceiver 46.

A portion 56 of the non-volatile memory 52 is allocated to storing sensor data. Accordingly, since the sensor node 22 includes data memory and digital processing capability, it can operate autonomously to acquire data even during intervals in which the wireless sensor network 20 is disconnected from the external monitor 30. Moreover, while only the sensor node 22 is illustrated in detail, it is to be appreciated that other sensor nodes 24, 26 of the autonomous wireless sensor network 20 similarly include one or more sensors, an internal power supply or power storage, a wireless transceiver, and digital processing and data storage capacity, and thus can operate autonomously. Moreover, in some embodiments the sensor nodes 22, 24, 26 operate cooperatively in a distributed computing mode by exchanging wireless messages. Thus, the autonomous wireless sensor network 20 can perform relatively complex operations, especially as the number of sensor nodes in the sensor network increases.

The sensors 22, 24, 26 of the sensor network 20 authenticate wireless communications amongst one another through the use of an association code that is tagged to the messages. As shown in FIG. 2 for the illustrative sensor 22, the association code 60 is suitably stored in an allocated portion of the non-volatile memory 52. The association code 60 is generated using a sensor that is common to all the sensor nodes 22, 24, 26. For example, if all the sensor nodes 22, 24, 26 include the ECG sensor 40, then the ECG signal can be used as a monitored characteristic of the medical subject 10 suitable for constructing the association code 60.

Figure 3:
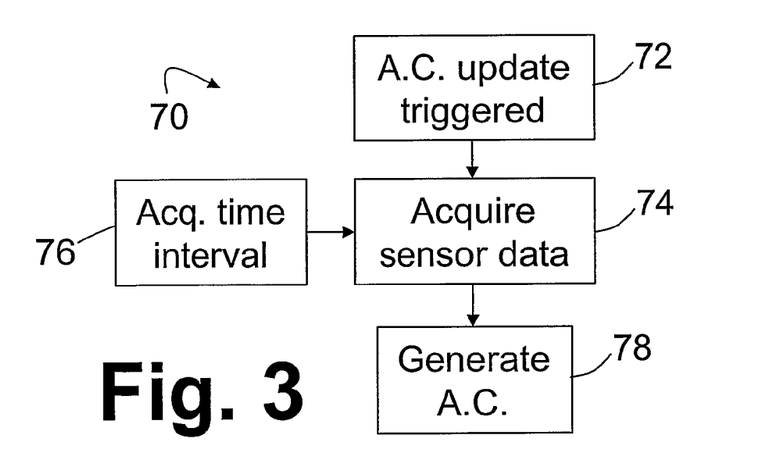
FIG. 3 flowcharts a process that executes substantially simultaneously on each of the wireless sensor nodes of the wireless autonomous sensor network of FIG. 1 to perform coordinated creation or updating of the association code.

The processor 50 is programmed to generate the association code 60 using a method 70 flowcharted in FIG. 3. The method 70 is performed substantially simultaneously by each of the sensor nodes 22, 24, 26. One of the sensor nodes 22, 24, 26 triggers an association code update in a process operation 72 by wirelessly transmitting an association code update request. Typically, an update request will be made when the sensor nodes 22, 24, 26 are first connected to the patient 10. The triggering operation 72 can also be triggered by a new sensor node that is added to the sensor network 20, or when one of the sensor nodes 22, 24, 26 detects removal of another sensor node from the network or other transmission failures or abnormalities. In some embodiments, the association code update process 70 is initiated periodically to ensure robust continued association of the sensor nodes 22, 24, 26 defining the sensor network 20.

Responsive to the triggering operation 72, each sensor node acquires sensor data of the commonly monitored characteristic, such as the example ECG characteristic, in a process operation 74 for an acquisition time interval 76. The acquisition time interval should be long enough to produce an acquired sensor data set that is uniquely attributable to the monitored medical subject 10. For the example ECG characteristic, the acquisition time interval 76 generally should span several heartbeats, that is, should be a few seconds or more. If another characteristic having a shorter or longer typical time response is employed, then the acquisition time interval 76 can be made correspondingly shorter or longer. Typically, the acquisition time interval 76 is either embedded in the software 54, or is included in the triggering message received in the triggering operation 72.

At each node 22, 24, 26, the association code 60 is generated from the acquired sensor data in a process operation 78. The association code 60 should be generated by processing the acquired sensor data to substantially suppress aspects of the sensor data that strongly depend upon the specific location or attachment of the sensor on the patient 10. Considering the example ECG characteristic, the amplitude of the electrocardiographic signal typically depends strongly upon where the sensor is placed and how well it is attached to the patient 10. Moreover, the ECG signal may have a substantial time delay depending upon where the sensor is placed. On the other hand, the general shape and periodicity (i.e., heart rate) of the ECG signal is typically substantially the same regardless of the location or attachment of the ECG sensor.

The acquired sensor data is typically a set of samples spanning the acquisition time interval 76. In one process for computing the association code 60 from the acquired sensor data, the set of sensor data samples are sub-sampled and amplitude-normalized to produce the association code 60. In another process for computing the association code 60, the set of sensor data samples are amplitude-normalized and Fourier transformed. As will be seen when corresponding message authentication processes are described, these example authentication codes are effective for producing an association code that uniquely identifies the patient 10 when the acquired sensor data is an ECG or other characteristic having a location-independent shape but location dependent amplitude and/or time lag.

Once the association code 60 is generated, it is stored in the memory 52. Subsequently, whenever a sensor node wirelessly transmits a message intended to be received by another sensor node or plurality of sensor nodes of the network 20, it attaches the stored association code 60 with the message as an association code tag, and wirelessly sends the message with the attached association code tag. At the receiving sensor node, the association code tag contained in the wirelessly received message is compared with the association code stored at the receiving sensor node in order to authenticate the message.

Figure 4:
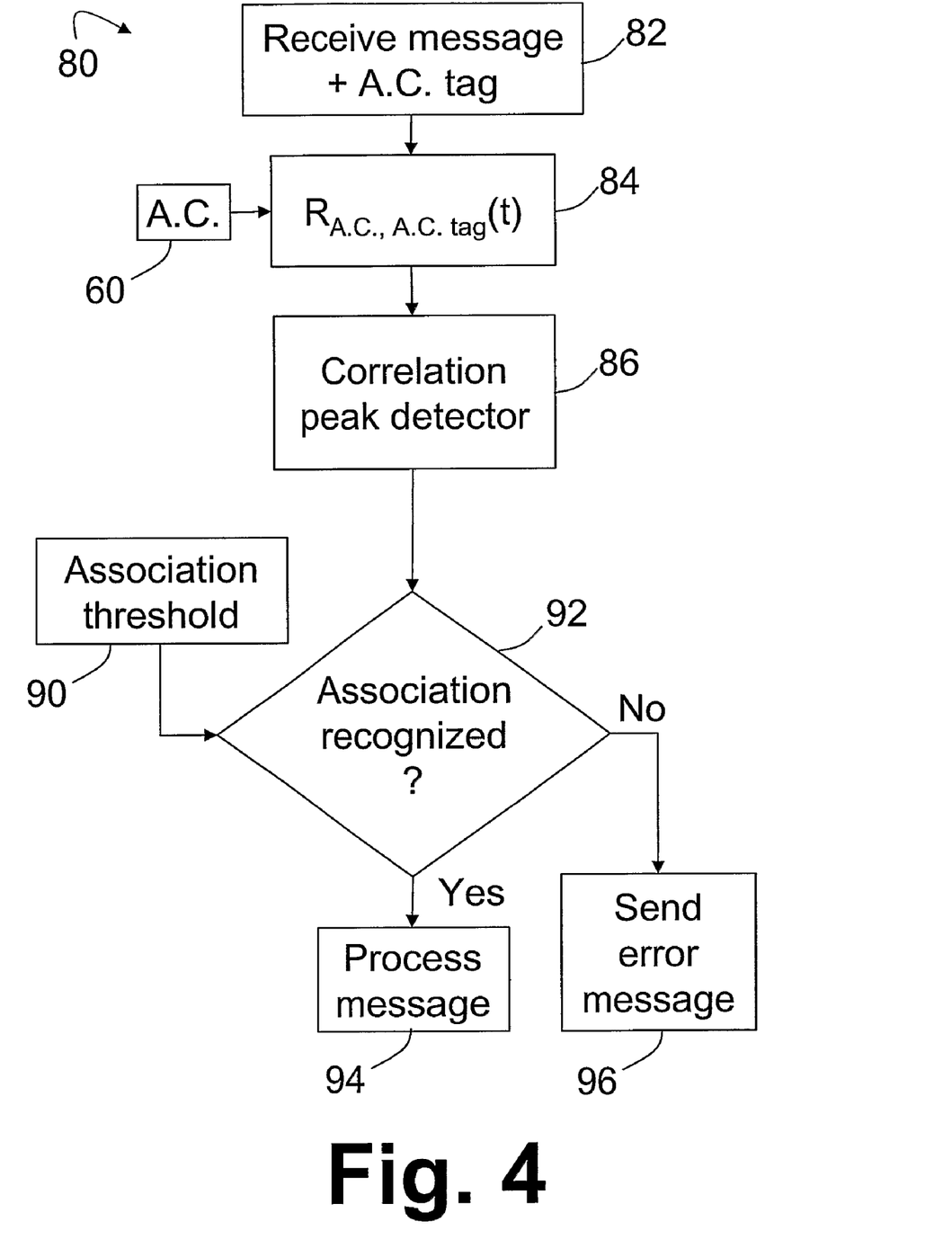
FIG. 4 flowcharts a message authentication process that executes on a wireless sensor node of the wireless autonomous sensor network of FIG. 1 when the sensor node receives a wireless message.

With reference to FIG. 4, a suitable example message authentication process 80 performed by the receiving sensor node is described. The authentication process 80 employs the example sub-sampled and amplitude-normalized association code 60. The sensor node receives a wireless message containing an association code tag in a process operation 82. The association code tag of the received message is correlated with the stored authentication code 60 using a suitable correlation. One suitable correlation function R[n] is:

$$R[n] = \sum_{i=0}^{M-1} A.C.[i] \cdot A.C.tag[n+i], \quad (1)$$
$$0 \le n < (2M-1),$$

where: A.C. is the stored association code 60 consisting of M sub-samples, A.C. tag is the association code tag of the received message which also consists of M sub-samples, the index i indexes the sub-samples, and the index n indexes the points of the correlation function R[n]. A correlation peak detection operation 86 detects the peak or maximum value of the correlation, such as the largest value of R[n] for the example Equation (1). At a given index n, the correlation R[n] corresponds to the integrated product of the association code 60 and the association code tag of the received message computed after shifting the association code tag by n data points. Accordingly, a relative time lead or lag of the acquired sensor data between the sending and receiving sensor nodes will merely result in a shift of the correlation peak position, but will generally not change the amplitude of the correlation peak.

Thus, any time lead or lag of the ECG or other characteristic used to construct the association code generally has little or no effect on the output of the correlation peak detection operation 86. Amplitude variations between the sending and receiving sensor nodes were previously accounted for by amplitude normalization in the example association code. Accordingly, the output of the correlation peak detection operation 86 is substantially independent of amplitude and time shift variations between the sending and receiving sensor nodes, and so the output of the correlation peak detection operation 86 is suitably compared with an association threshold 90 in a comparison operation 92 to authenticate the received message (that is, to decide whether or not the received message is from one of the sensor nodes of the sensor network 20). If the comparison operation 92 authenticates the message, then the message is processed in a processing operation 94. For example, if the message is a command, it is executed by the receiving sensor node; if the message is data it is stored or otherwise utilized by the receiving sensor node. If the comparison operation 92 fails to authenticate the message, then an error message is optionally wirelessly sent in an error operation 96. In some embodiments employing an ECG characteristic that is normalized and sub-sampled to generate the association code 60, and which further employ a correlation comparison, the threshold 90 for authentication is typically between about 95% to 98% correlation.

In embodiments in which the authorization code 60 is computed by amplitude-normalizing and Fourier transforming the acquired sensor data, the correlation operation 84 is suitably replaced by a multiplicative combination of the association code 60 and the association code tag. For example, the set of sensor data samples can be amplitude-normalized and processed by a fast Fourier transform (FFT) to produce a plurality of Fourier frequency data points defining the association code 60. The correlation operation 84 is then suitably replaced by a pointwise multiplying of corresponding frequency values of the association code 60 and the association code tag of the message, and the peak detector 86 identifies the largest Fourier frequency amplitude. For a periodic characteristic such as the ECG signal, the largest Fourier frequency amplitude occurs at about the pulse rate frequency. Using this approach the output of the peak detector 86 is again substantially unaffected by amplitude differences or time shift between the acquired sensor data of the sending and receiving sensor nodes used in constructing the association code at each sensor node.

All of the sensor nodes 22, 24, 26 of the sensor network 20 monitor a common characteristic of the patient 10, such as the ECG. In some sensor networks, however, there may be no single characteristic which is monitored by all the sensor nodes of the network. In some such situations, the disclosed association approach can be extended by using a sensor node that monitors two different characteristics to relay messages between a first group of sensor nodes having sensors that monitor the first characteristic but not the second characteristic and a second group of sensor nodes having sensors that monitor the second characteristic but not the first characteristic.

Figure 5:
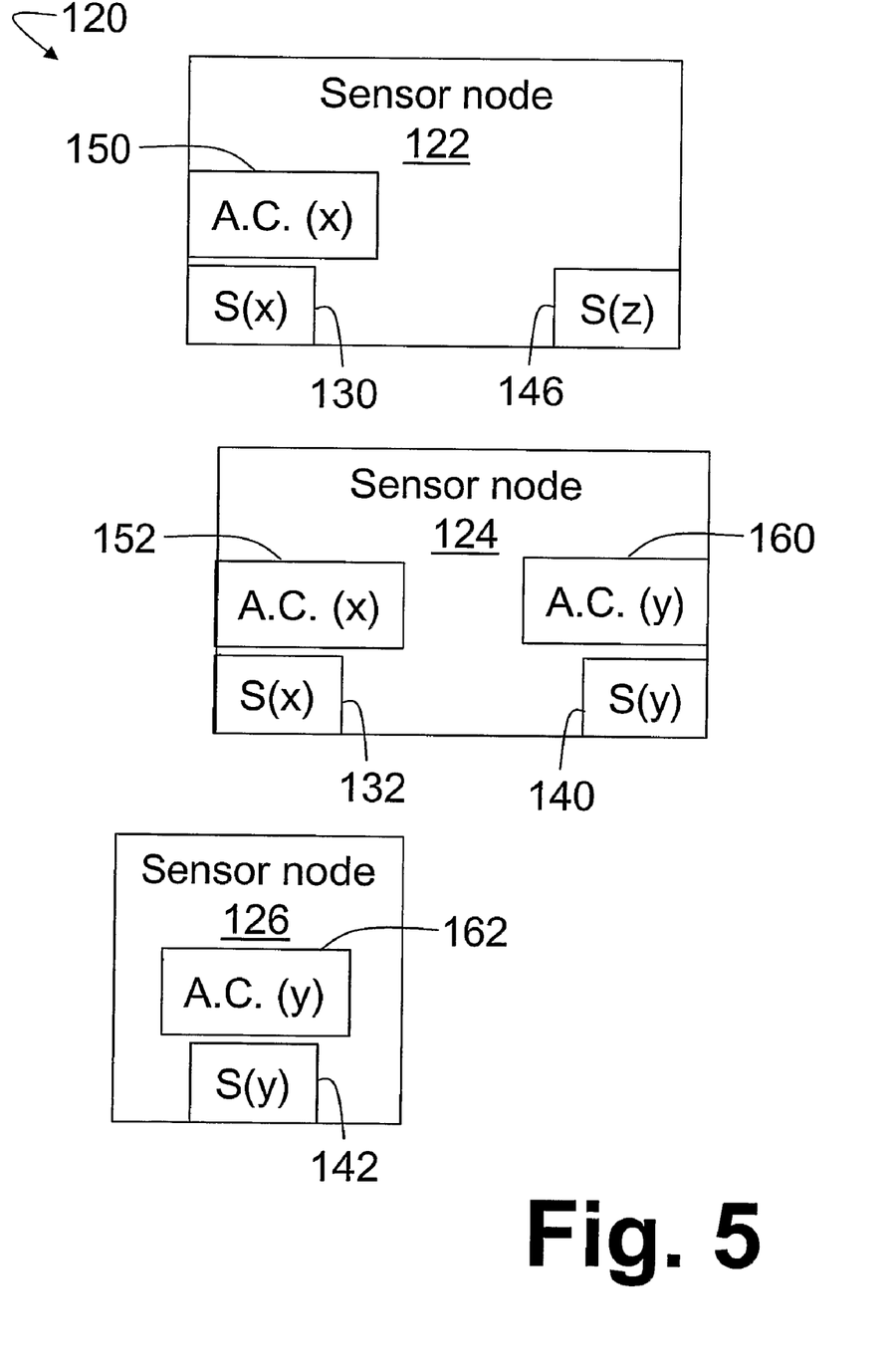
FIG. 5 diagrammatically illustrates a sensor network including three sensor nodes, one of which provides message relaying between the other two sensor nodes.

With reference to FIG. 5, an example of such a relay approach is described. A sensor network 120 includes sensor nodes 122, 124, 126 all monitoring a single medical subject. The sensor nodes 122, 124 have sensors 130, 132, respectively, that monitor a characteristic "x" of the medical subject. The sensor nodes 124, 126 have sensors 140, 142, respectively, that monitor a characteristic "y" of the medical subject. The sensor node 122 also includes a sensor 146 that monitors a characteristic "z" of the medical subject. The monitored characteristics "x" and "y" are used in authenticated message relaying between the sensor nodes 122, 126.

Although there is no single characteristic that is monitored by all three sensor nodes 122, 124, 126, the sensor node 124 can serve as a relay node for the sensor network 120, because it monitors at least one characteristic in common with each of the other sensor nodes 122, 126. In the illustrated example, the sensor nodes 122, 124 each generate an association code designated "A.C.(x)" in accordance with the process 70 of FIG. 3 using the characteristic "x". One "A.C.(x)" association code 150 is computed and stored on the sensor node 122, and another "A.C.(x)" association code 152 is computed and stored on the sensor node 124. Thus, the sensor nodes 122, 124 can perform message authentication between each other using the "A.C.(x)" association code. Similarly, the sensor nodes 124, 126 each generate an association code designated "A.C.(y)" in accordance with the process 70 of FIG. 3 using the characteristic "y". One "A.C.(y)" association code 160 is computed and stored on the sensor node 124, and another "A.C.(y)" association code 162 is computed and stored on the sensor node 126. Thus, the sensor nodes 124, 126 can perform message authentication between each other using the "A.C.(y)" association code. When using a relay node, the type of association code must be communicated or known to the sensors involved in the relay. In one approach, an indication of the type of characteristic from which the association code is transmitted along with the association code. For example, a one-byte identifier can be generated that characterizes the type of derived association code, and this identifier can then be transmitted together with the association code. In another approach, each sensor can maintain a list or table of the association code types of all other sensors.

Moreover, the sensor node 124 can relay messages from the sensor node 122 to the sensor node 126. To do so, the sensor node 124 receives and authenticates a message from the sensor node 122 in the usual way, for example in accordance with the method 80 of FIG. 4. Once authenticated, the sensor node 124 modifies the received message by replacing the "A.C.(x)" association code tag of the message with the "A.C.(y)" association code 160 stored on the sensor node 124, and wirelessly sends the modified message. At the sensor node 126, authentication of the message originally sent by the sensor node 122 fails since the association code and the association code tag of the message employ different characteristics "x" and "y". However, the modified message sent by the relay sensor node 124 is received and successfully authenticated by the sensor node 126, since in the case of the modified message both the association code and the association code tag of the modified message employ the same characteristic "y". In similar fashion, a message sent by the sensor node 126 using the association code "A.C.(y)" 162 fails authentication at the sensor node 122; however, it is successfully authenticated at the relay sensor node 124 using the association code "A.C.(y)" 160 stored at the relay sensor node 124. The message is then modified at the relay sensor node 124 by replacing the "A.C.(y)" association code tag with the association code "A.C.(x)" 152 and the modified message is sent, received and authenticated at the sensor node 122.

The described relaying can readily be extended to more than three sensor nodes, and in some embodiments there may be more than one relay sensor node to provide relaying between different groups of sensor nodes that authenticate based on different characteristics of the medical subject. For example, if additional sensor nodes are added which monitor only characteristic "z", then the sensor node 122 can be adapted to relay messages to those nodes by computing an association code "A.C.(z)" (not shown in FIG. 5). Messages tagged with "A.C.(x)" would be relayed by the adapted sensor node 122 by replacing the "A.C.(x)" tag with the "A.C.(z)" association code and sending the modified message. Messages tagged with "A.C.(z)" would be relayed by the adapted sensor node 122 by replacing the "A.C.(z)" tag with the "A.C.(x)" association code and sending the modified message.

In the sensor network 120, the relay sensor node 124 performs the specialized task of relaying messages between sensor nodes or groups of sensor nodes that do not monitor common characteristics of the medical subject. Similarly, certain nodes of the sensor network 120 can be designated to perform other specialized tasks. For example, the sensor node 124 may also collect and send sensor data from all three sensor nodes 122, 124, 126 to the external monitor 30. In other embodiments, the sensor nodes of a sensor network define a distributed computing structure having no particular specialized sensor nodes. Alternatively, the vital sign-based association code can be combined with non-vital sign-based encoding such as a department code, a procedure code, a time stamp, other fixed or variable identification codes, and the like.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A wireless sensor network for wirelessly monitoring a medical subject, the wireless sensor network comprising:
   a plurality of sensor nodes, each sensor node including a wireless transceiver for sending and receiving wireless messages, a sensor monitoring a characteristic of the medical subject, and a processor programmed to at least perform an authentication method including:
   (i) acquiring sensor data via the sensor for a predetermined time responsive to receiving a wireless trigger message,
   (ii) storing an association code computed from the acquired sensor data, and
   (iii) authenticating a subsequently received wireless message containing an association code tag by comparing the association code tag with the stored association code.

2. The wireless sensor network as set forth in claim 1, wherein the processor is further programmed to perform a wireless message sending method including:
   attaching the stored association code with a message as an association code tag, and
   wirelessly sending the message including the attached association code tag,
at least one other sensor node receiving the wirelessly sent message including the attached association code tag and performing the authenticating (iii) to authenticate the received message including the attached association code tag.

3. The wireless sensor network as set forth in claim 1, wherein the association code includes a data set derived from the acquired sensor data, and the authenticating includes:
computing a correlation of the association code and the association code tag; and
comparing the correlation with a predetermined authentication standard.

4. The wireless sensor network as set forth in claim 3, wherein the comparing includes:
determining a peak of the correlation; and
comparing the peak with an authentication peak threshold.

5. The wireless sensor network as set forth in claim 1, wherein the computing of the association code from the acquired sensor data includes Fourier transforming the acquired sensor data, and the authenticating includes:
computing a multiplicative combination of the association code and the association code tag; and
comparing the multiplicative combination with a predetermined authentication standard.

6. The wireless sensor network as set forth in claim 1, wherein the computing of the association code from the acquired sensor data includes Fourier transforming the acquired sensor data, and the authenticating includes:
pointwise multiplying Fourier frequencies of the association code and the association code tag to produce a pointwise product data set;
determining a peak of the pointwise product data set; and
comparing the peak with an authentication peak threshold.

7. The wireless sensor network as set forth in claim 1, wherein (i) the acquired sensor data includes a set of samples spanning the predetermined time, and (ii) the association code includes a plurality of data points computed from the set of samples.

8. The wireless sensor network as set forth in claim 7, wherein the plurality of data points are computed by amplitude normalizing the set of samples.

9. The wireless sensor network as set forth in claim 7, wherein the plurality of data points are computed by subsampling the set of samples.

10. The wireless sensor network as set forth in claim 7, wherein the plurality of data points are computed by Fourier transforming the set of samples.

11. The wireless sensor network as set forth in claim 1, wherein:
at least a first sensor node of the plurality of sensor nodes include a sensor monitoring a first characteristic of the medical subject but does not include a sensor monitoring a second characteristic of the medical subject, the authentication method of the first sensor node employing the sensor monitoring the first characteristic;
at least a second sensor node of the plurality of sensor nodes include a sensor monitoring the second characteristic of the medical subject but does not include a sensor monitoring the first characteristic of the medical subject, the authentication method of the second sensor node employing the sensor monitoring the second characteristic, and
at least a third sensor node of the plurality of sensor nodes includes sensors monitoring both the first and second characteristics of the medical subject, the processor of the third sensor node being programmed to perform the authentication method to generate first and second stored association codes corresponding to the first and second characteristics and further performing a message relay method including:
(iv) subsequent to authenticating a received wireless message containing an association code tag corresponding to one of the stored first association code and the stored second association code, modifying the message by replacing the tag with the other of the first association code and the second association code, and
(v) wirelessly sending the modified message.

12. The wireless sensor network as set forth in claim 1, wherein the plurality of sensor nodes define an autonomous wireless sensor network that autonomously: (i) acquires and stores sensor data pertaining to a plurality of characteristics of the medical subject, and (ii) wirelessly transmits the stored sensor data to an external device.

13. The wireless sensor network as set forth in claim 1, wherein at least one of the plurality of sensor nodes includes:
a data memory storing sensor data pertaining to the monitoring of the characteristic of the medical subject, the processor being further programmed to perform a data dump method including:
constructing a data message containing stored sensor data pertaining to the monitoring of the characteristic of the medical subject,
attaching the stored association code with the data message as an association code tag, and
wirelessly sending the data message with the attached association code tag,
the data dump method being performed responsive to receiving and authenticating a wireless data dump request message.

14. The wireless sensor network as set forth in claim 1, wherein at least one sensor of the plurality of sensor nodes includes:
a second sensor monitoring a second characteristic of the medical subject that is different from the characteristic monitored by the other sensor; and
a data memory storing sensor data pertaining to the monitoring of the second characteristic of the medical subject, the processor being further programmed to perform a data dump method including:
constructing a data message containing stored second sensor data pertaining to the monitoring of the characteristic of the medical subject,
attaching the stored association code with the data message as an association code tag, and
wirelessly sending the data message with the attached association code tag,
the data dump method being performed responsive to receiving and authenticating a wireless data dump request message.

15. A wireless sensor node for use in the network of claim 1.

16. A wireless sensor network method performed by a plurality of sensor nodes wirelessly monitoring a medical subject, the wireless sensor network method comprising:
performing at each sensor node an authentication process including:
(i) acquiring sensor data pertaining to a characteristic of the medical subject for a predetermined time responsive to a receiving wireless trigger message,
(ii) storing an association code identifying the medical subject, the association code being computed from the acquired sensor data, and
(iii) authenticating that a subsequently received wireless message containing an association code tag is associated with the medical subject by comparing the association code tag with the stored association code.

17. The wireless sensor network method as set forth in claim 16, further including:
performing at a sensor node a wireless message send process including:

attaching the stored association code to a message as an association code tag, and wirelessly sending the message including the attached association code tag, at least one other sensor node receiving the wirelessly sent message including the attached association code tag and performing the authenticating (iii) to authenticate the received message including the attached association code tag.

18. The wireless sensor network method as set forth in claim 16, wherein the association code includes a data set derived from the acquired sensor data, and the authenticating includes:

combining the association code and the association code tag to generate an authentication measure using one of (ii) a correlation and (ii) Fourier transforming and multiplying of the association code and the association code tag; and comparing the authentication measure with a predetermined authentication standard.

19. The wireless sensor method as set forth in claim 16, further including:

acquiring and storing sensor data pertaining to a plurality of characteristics of the medical subject, and wirelessly transmitting the stored sensor data to an external device.

20. The wireless sensor method as set forth in claim 19, wherein the plurality of characteristics that are acquired, stored, and wirelessly transmitted include the characteristic used in the authentication process.

21. A wireless sensor network for wirelessly monitoring a medical subject, the wireless sensor network comprising:

a plurality of sensor nodes, each sensor node including a wireless transceiver for sending and receiving wireless messages, a sensor monitoring a characteristic of the medical subject, and a processor programmed to at least perform an authentication method including:
  (i) acquiring sensor data pertaining to the characteristic of the medical subject via the sensor for a predetermined time responsive to receiving a wireless trigger message,
  (ii) computing an association code identifying the medical subject from the acquired sensor data,
  (iii) storing the computed association code at the sensor, and
  (iv) authenticating that a wireless message subsequently received by the sensor node is associated with the medical subject by comparing an association code tag contained in the received wireless message with the stored association code.

* * * * *